(12) United States Patent
Gottschaldt et al.

(10) Patent No.: US 11,530,296 B2
(45) Date of Patent: Dec. 20, 2022

(54) CATIONIC POLYMERS WITH D-FRUCTOSE SUBSTITUENTS

(71) Applicant: Friedrich-Schiller-Universitaet Jena, Jena (DE)

(72) Inventors: Michael Gottschaldt, Beutnitz (DE); Michael Proehl, Jena (DE); Christoph Englert, Jena (DE); Ulrich Sigmar Schubert, Jena (DE)

(73) Assignee: FRIEDRICH-SCHILLER-UNIVERSITAET JENA, Jena (DE)

( * ) Notice: Subject to any disclaimer, the term of this patent is extended or adjusted under 35 U.S.C. 154(b) by 296 days.

(21) Appl. No.: 16/495,676

(22) PCT Filed: Mar. 23, 2018

(86) PCT No.: PCT/DE2018/100268
§ 371 (c)(1),
(2) Date: Jan. 30, 2020

(87) PCT Pub. No.: WO2018/171845
PCT Pub. Date: Sep. 27, 2018

(65) Prior Publication Data
US 2020/0407502 A1 Dec. 31, 2020

(30) Foreign Application Priority Data
Mar. 23, 2017 (DE) .......................... 102017003004.9

(51) Int. Cl.
C08G 69/48 (2006.01)
A61K 47/64 (2017.01)
A61K 47/54 (2017.01)
C07H 3/02 (2006.01)
C08G 73/02 (2006.01)

(52) U.S. Cl.
CPC .......... *C08G 69/48* (2013.01); *A61K 47/543* (2017.08); *A61K 47/6455* (2017.08); *C07H 3/02* (2013.01); *C08G 73/0226* (2013.01)

(58) Field of Classification Search
CPC ............... C08G 69/48; C08G 73/0226; A61K 47/6455; A61K 47/543; C07H 3/02
See application file for complete search history.

(56) References Cited

U.S. PATENT DOCUMENTS

| | | | | |
|---|---|---|---|---|
| 2003/0018002 | A1* | 1/2003 | Sagara | A61K 48/0041 514/44 R |
| 2005/0027064 | A1* | 2/2005 | Lynn | C08L 79/02 524/555 |
| 2006/0093674 | A1 | 5/2006 | Slobodkin | |
| 2008/0281064 | A1 | 11/2008 | Chiron | |

FOREIGN PATENT DOCUMENTS

| | | |
|---|---|---|
| DE | 19605355 A1 | 8/1997 |
| WO | 2003008555 A2 | 1/2003 |
| WO | 2016178233 A1 | 11/2016 |

OTHER PUBLICATIONS

Google_Scholar_search-1-14-22_polyethyleneimine_gene_carrier_fructose.pdf (Year: 2022).*
Google_Scholar_search-1-14-22_polyethyleneimine_gene_carrier_thioethe_linkage_sugar.pdf (Year: 2022).*
Google_Scholar_search-1-14-22_polyethyleneimine_gene_carrier_thiol_linkage.pdf (Year: 2022).*
Google_Scholar_search-1-14-22_substituted_fructose_targeting_moiety_cationic_polymer.pdf (Year: 2022).*
Google_Scholar-1-6-22_fructose_bonded_to_cationic_polymer.pdf (Year: 2022).*
STIC_Search_16495676_01-10-2022.pdf (Year: 2022).*
H. Lv et al. (2006): "Toxicity of cationic lipids and cationic polymers in gene delivery" Journal of Controlled Release 114: 100-109).
CL Waite et al. (2009): "PAMAM-RGD Conjugates Enhance siRNA Delivery Through a Multicellular Spheroid Model of Malignant Glioma" Bioconjugate Chemistry: 20: 1908-1916.

(Continued)

*Primary Examiner* — Michael P Cohen
(74) *Attorney, Agent, or Firm* — Abel Schillinger, LLP

(57) ABSTRACT

The invention relates to new cationic polymers conjugated with D-fructose, as a result of which they can selectively interact with specific structure elements on cell surfaces. The problem was that of creating novel, biocompatible, easy-to-produce, D-fructose-conjugated cationic polymers that have a higher selectivity with respect to certain cell types. To solve this problem, the invention proposes cationic polymers with covalently bonded D-fructose of general formula (I) with the following components: a) cationic polymer: macromolecular compounds of n repeat units with one or more positive charges; b) linker: a unit that links the cationic polymer with D-fructose or derivatives of D-fructose by means of any alkyl or aryl group, any alkenyl or alkinyl group, an ether, thioether or amine, an ester, amide or other carboxylic acid derivative, a heterocycle (e.g. triazole or m maleimide), a disulphide, an imine or an imide; c) D-fructose: one or more D-fructoses or D-fructose derivatives in an open-chain, furanoid or pyranoid structure, not glycosidically linked via one of the five possible carbon atoms (1, 3, 4, 5, 6).

17 Claims, 5 Drawing Sheets

(56) References Cited

OTHER PUBLICATIONS

T. Dutta et al (2007): "Targeting potential and anti-HIV activity of lamivudine loaded mannosylated poly(propyleneimine) dendrimer" Biochimica et Biophysica Acta (BBA)—General Subjects: 1770, 681-686.

Kazyyoshi Sagara; publication: K. Sagara et al. (2002). "A new synthesis of galactose-poly(ethylene glycol)polyethyleneimines for gene delivery to hepatocytes" Journal of Controlled Release 79 (1-3): 271-281.

Y. Hayashi et al (2012): "Potential Use of Lactosylated Dendrimer (G3)/α-Cyclodextrin Conjugates as Hepatocyte-Specific siRNA Carriers for the Treatment of Familial Amyloidotic Polyneuropathy" Molecular Pharmaceutics: 9, 1645-1653).

Huang, H. et al. (2009): "Suppressive effects of sugar-modified cationic liposomes/NF-κB decoy complexes on adenovirus vector-induced innate immune responses" Journal of Controlled Release: 133, 139-145).

A. Godoy et al. (2006): Differential subcellular distribution of glucose transporters GLUT1-6 and GLUT9 in human Dancer: Ultrastructural localization of GLUT1 and GLUT5 in breast tumor tissues. Journal of Cellular Physiology 207(3): 614-627).

\* cited by examiner

CATIONIC POLYMERS WITH D-FRUCTOSE SUBSTITUENTS

FIELD OF THE DISCLOSURE

The invention relates to new cationic polymers conjugated with D-fructose which can selectively interact with specific structure elements on cell surfaces.

BACKGROUND

Known cationic polymers, such as poly(ethyleneimine) (PEI) or poly-L-lysine (PLL), have significant disadvantages (H. Lv et al. (2006): "Toxicity of cationic lipids and cationic polymers in gene delivery" *Journal of Controlled Release* 114: 100-109):
   general and non-specific cytotoxicity to cells,
   triggering aggregation and hemolysis of blood cells.

Cationic polymers have the ability to complex negatively charged, genetic material, such as siRNA (small interfering ribonucleic acid) or pDNA (plasmid desoxyribonucleic acid), due to their high density of positive charges. The resulting adducts between cationic polymers and genetic material are called polyplexes, which can help to transport genetic material (e.g. siRNA) into cells.

Cationic polymers have already been used successfully as an additive in sugar surfactants for improving the sensory properties and the foam sensation in cosmetic applications (patent application: Use of cationic biopolymers to improve the sensory properties of sugar surfactant-containing preparations, DE19605355A1, Joerg Kahre, Rolf Wachter).

Furthermore, cationic polymers can be functionalized with small protein sequences (e.g.: RGD peptides) and thus the selectivity can be influenced (C L Waite et al. (2009): "PAMAM-RGD Conjugates Enhance siRNA Delivery Through a Multicellular Spheroid Model of Malignant Glioma" *Bioconjugate Chemistry:* 20: 1908-1916). The exact mechanism is unclear and the presence of integrin (transport membrane protein in animal cells) is necessary.

A covalent linkage of cationic polymers with sugars has also become known.

Poly(propyleneimine) polymers could be functionalized with D-mannose and their properties studied in successful use against HIV. This approach is used exclusively for the targeted activation of immune cells, so-called macrophages, with lectin receptors. (T. Dutta et al (2007): "Targeting potential and anti-HIV activity of lamivudine loaded mannosylated poly(propyleneimine) dendrimer" Biochimica et Biophysica Acta (BBA)—General Subjects: 1770, 681-686).

The synthesis of D-galactose-conjugated poly(ethylene glycol) poly(ethyleneimine) copolymers for the transfection of genetic material into hepatocytes has been described. This approach is only suitable for liver cells which have ASGP receptors (patent application: Cellular targeting poly(ethylene glycol)-grafted polymeric gene carrier, WO2003008555A2, Kazyyoshi Sagara; publication: K. Sagara et al. (2002). "A new synthesis of galactose-poly (ethylene glycol) polyethyleneimines for gene delivery to hepatocytes" *Journal of Controlled Release* 79 (1-3): 271-281).

Lactose and α-cyclodextrin were coupled to a cationic, star-shaped poly(amidoamine) (PAMAM) dendrimer for the treatment of familial, amyloidotic polyneuropathy. The approach aims only at the transthyretin gene expression in hepatocytes (Y. Hayashi et al (2012): "Potential Use of Lactosylated Dendrimer (G3)/α-Cyclodextrin Conjugates as Hepatocyte-Specific siRNA Carriers for the Treatment of Familial Amyloidotic Polyneuropathy" *Molecular Pharmaceutics:* 9, 1645-1653).

Cationic liposomes were modified with D-fucose and examined for their influence on adenovirus-induced immune responses. This approach is exclusively for targeted delivery of the specific transcription factor NF-κB to spleen and liver macrophages. (Huang, H. et al. (2009): "Suppressive effects of sugar-modified cationic liposomes/NF-κB decoy complexes on adenovirus vector-induced innate immune responses" *Journal of Controlled Release:* 133, 139-145).

Acrylate- or methacrylate-based cationic polymers comprising glycosidically bound saccharides have been described. The approach describes only the chemical composition of such polymers and in no way mentions a possible biological application. With the glycosidically bound sugar residues described there, an interaction with sugar transporters in cell membranes cannot be achieved (patent application: Novel Glycopolymers, Uses Thereof, and Monomers Useful for Preparation Thereof, US20080281064A1, Stephanie Chiron, Marie-Pierre LaBeau, Etienne Fleury, David Viet, Sylvain Cottaz, Hugues Driguez, Sami Halila).

Nucleic acids and their polyplexes with cationic polymers have been described. In this approach, sugar molecules were present in solution in polyplex formation, but are not covalently bound to the cationic polymer. So they do not fulfill any direct targeting functions. (Patent application: Nucleic acid-cationic polymer compositions and methods of making and using the same, WO2016178233A1, Abraham Hochberg, Jennifer Gallula).

SUMMARY OF THE INVENTION

The aim of the invention is to provide novel, biocompatible, easily producible, D-fructose-conjugated cationic polymers having an increased selectivity with respect to certain cell types.

The term selectivity relates in one aspect to the interaction of novel D-fructose-conjugated, cationic polymers with certain structural elements on the cell surface and, in another aspect, to the cytotoxic effect on certain cell types. A non-limiting example of particular interest is herein the selective, cytotoxic effect on GLUT5-overexpressing cell types, such as, for example, a majority of breast cancer cell types.

According to the invention, cationic polymers having D-fructose substituents are found to solve this problem which contain general formula (I) as basic structure.

The cationic polymer herein is a macromolecular compound of n repeating units (preferably n=10 to 1000) having one or more positive charges.

Non-limiting examples of preferred cationic polymers can include poly-L-lysine (PLL), polyethylenimine (PEI) or dextrans such as diethylaminoethyl-dextran (DEAE-D) or dextran-spermine (D-SPM) or polymethacrylates such as poly(2-dimethylaminoethyl methacrylate) (PDMAEMA) and poly(dimethylaminoethyl methacrylate) (PDAMA).

Linkers are herein one or more atoms or functional groups that connect the cationic polymer to the D-fructose unit. Suitable for this purpose are, for example, any alkyl or aryl residue, any alkenyl or alkynyl residue, an ether or thioether, an amine, an ester-, amide- or another carboxylic acid derivative, a heterocycle (e.g. triazole or maleimide), a disulfide, an imine or an imide.

Under D-fructose and its derivatives are understood all chemical molecules which are based on D-fructose and maintain the stereochemistry at positions 3, 4 and 5 in open or closed form.

Chemical modifications, in particular the introduction of functional groups, such as thiol, azide, carboxylic acids and their derivatives and/or amino groups, to one or more positions of the sugar (but not at the glycosidic C2 atom of the D-fructose), while maintaining the stereochemistry of positions 3, 4 and 5 are herein also understood as D-fructose derivatives.

D-fructose has a keto functionality in open-chain form which completely changes the chemical properties. It is, like in other sugars, introduced into the cells via specific transport proteins (GLUTs) and metabolized. The transporter responsible for D-fructose is the GLUT5 transporter (A. Godoy et al. (2006): Differential subcellular distribution of glucose transporters GLUT1-6 and GLUT9 in human cancer: Ultrastructural localization of GLUT1 and GLUT5 in breast tumor tissues." Journal of Cellular Physiology 207 (3): 614-627).

Surprisingly, the D-fructose-substituted, cationic polymer P3 has shown to be advantageous:

In comparison to unmodified, cationic polymers (e.g. L-PEI), P3 contains:
- an increased water solubility;
- cytotoxicity to breast cancer cells, such as MDA-MB-231;
- no cytotoxicity to non-cancer cells, such as HUVEC or L929;
- greatly reduced hemolytic activity with respect to blood cells;
- no triggering of the aggregation of blood components;

and the ability to form polyplexes with negatively charged biomolecules, such as pDNA or siRNA.

BRIEF DESCRIPTION OF THE DRAWINGS

Embodiments are illustrated by way of example and are not limited in the accompanying figures.

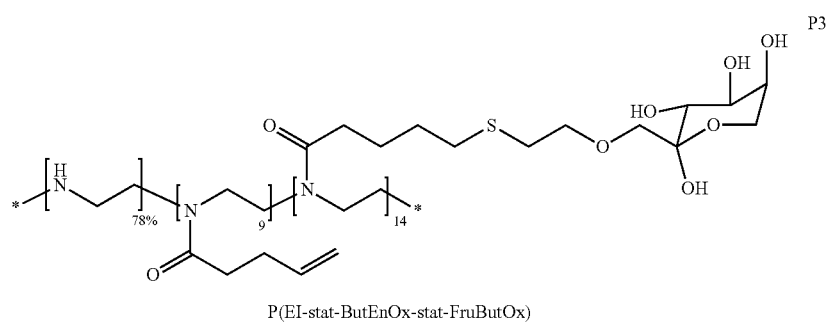

P(EI-stat-ButEnOx-stat-FruButOx)

DETAILED DESCRIPTION

Figure 1:
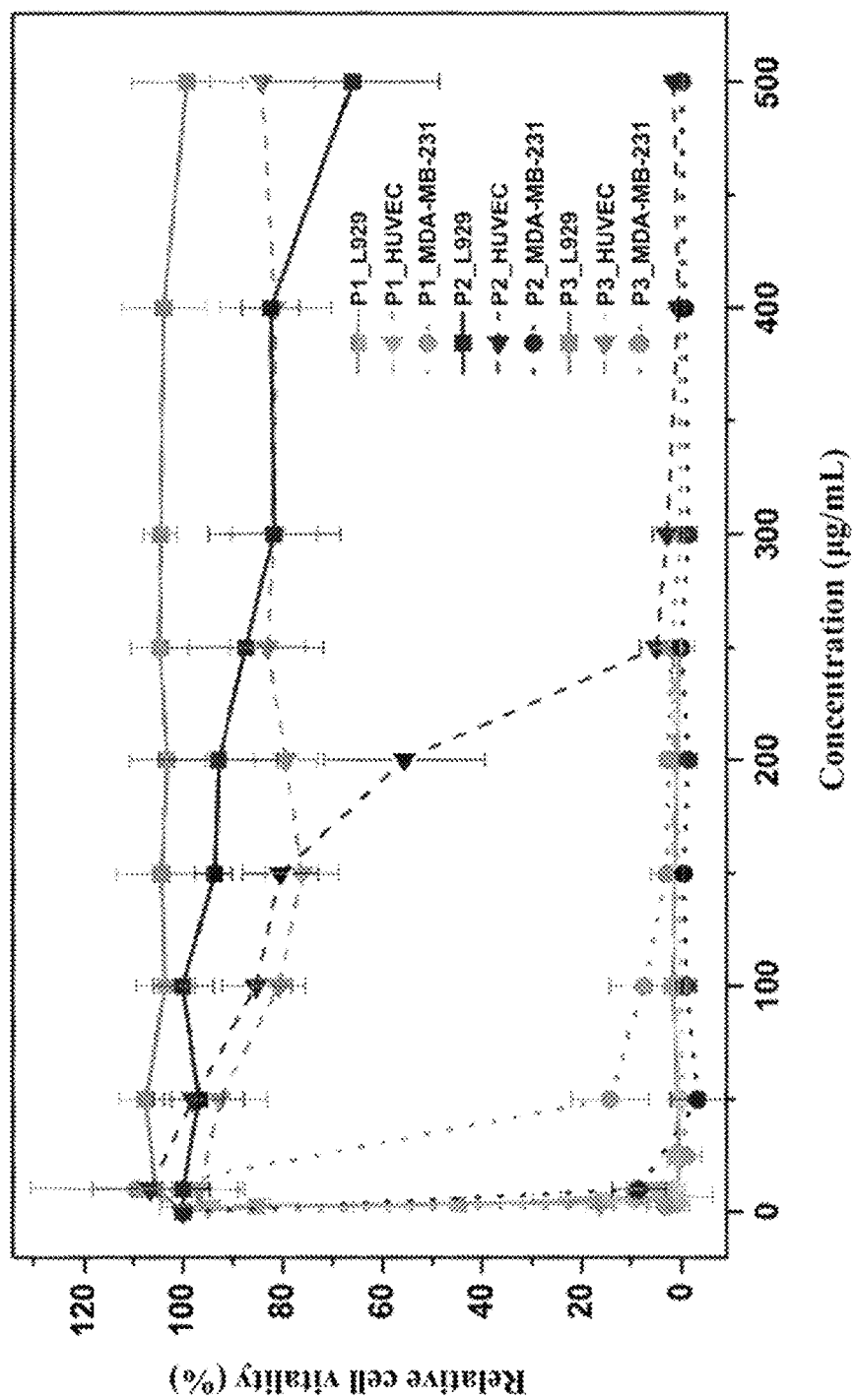
FIG. 1 includes a graph illustrating cell type dependent cytotoxicity studies of polymers P1, P2, and P3 according to embodiments.

The invention is illustrated in the following by the synthesis of D-fructose-conjugated cationic polymers (based on linear poly(ethyleneimine) (L-PEI, (I)) and branched poly (ethyleneimine) (B-PEI, (II)).

(I) Synthesis of D-Fructose-Conjugated (Unbranched) L-PEI

1. Synthesis of the SH-Functionalized D-Fructose Derivative in a Four-Step Synthesis

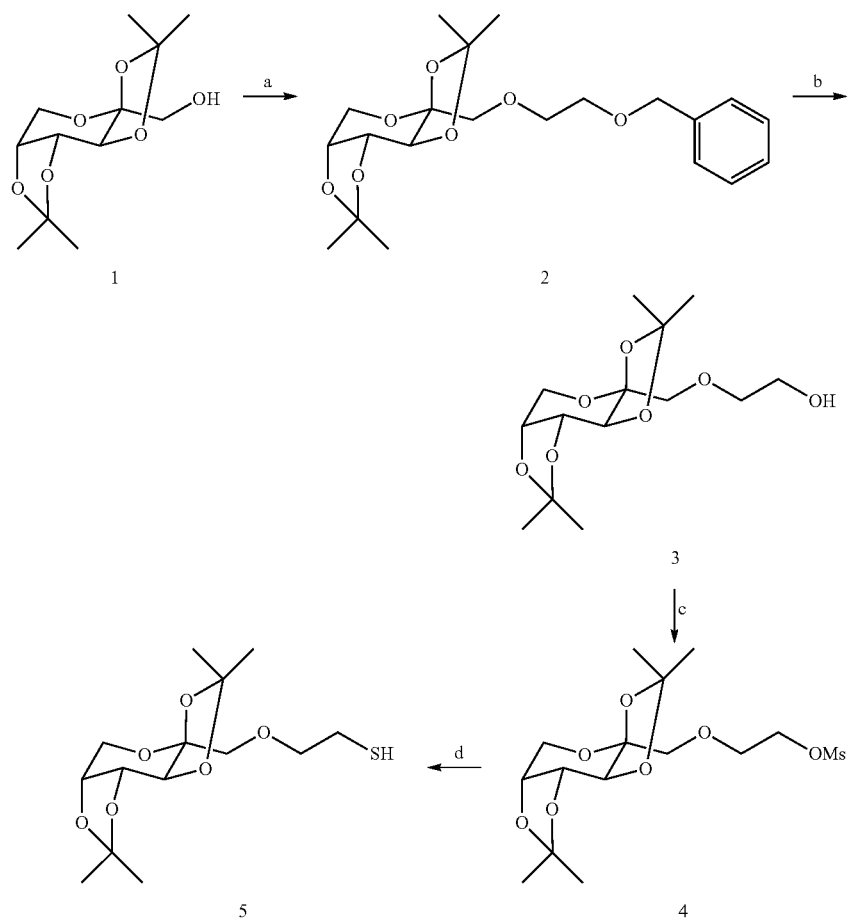 [SMILES: CC1(C)OC2COC3(CO)OC(C)(C)OC3C2O1 ; CC1(C)OC2COC3(COCCOCc4ccccc4)OC(C)(C)OC3C2O1 ; CC1(C)OC2COC3(COCCO)OC(C)(C)OC3C2O1 ; CC1(C)OC2COC3(COCCS)OC(C)(C)OC3C2O1 ; CC1(C)OC2COC3(COCCOS(C)(=O)=O)OC(C)(C)OC3C2O1]

Schematic representation of the four-step synthesis of 1-O-(2-mercapto-ethyl)-2,3:4,5-di-O-isopropylidene-β-D-fructopyranoside: a) Benzyl 2-bromoethyl ether, NaH, THF, rt; b) $H_2$/Pd (C), $CH_3OH$, rt; c) mesyl chloride, $Et_3N$, 4-DMAP, $CH_2Cl_2$, 0° C.; d) 1. Thiourea, butanone, 95° C., 2. $K_2S_2O_5$, $CH_2Cl_2/H_2O$, 50° C.

The D-fructose derivative 5 was fully characterized and all individual steps could be performed in high yields. The introduction of the thiol serves to attach the sugar to the polymer via a photocatalyzed thiol-ene click reaction.

2. Synthesis of the Block Copolymer Followed by Thiol-Ene Click Between D-Fructose and Polymer Precursor and Deprotection of the Sugar Unit

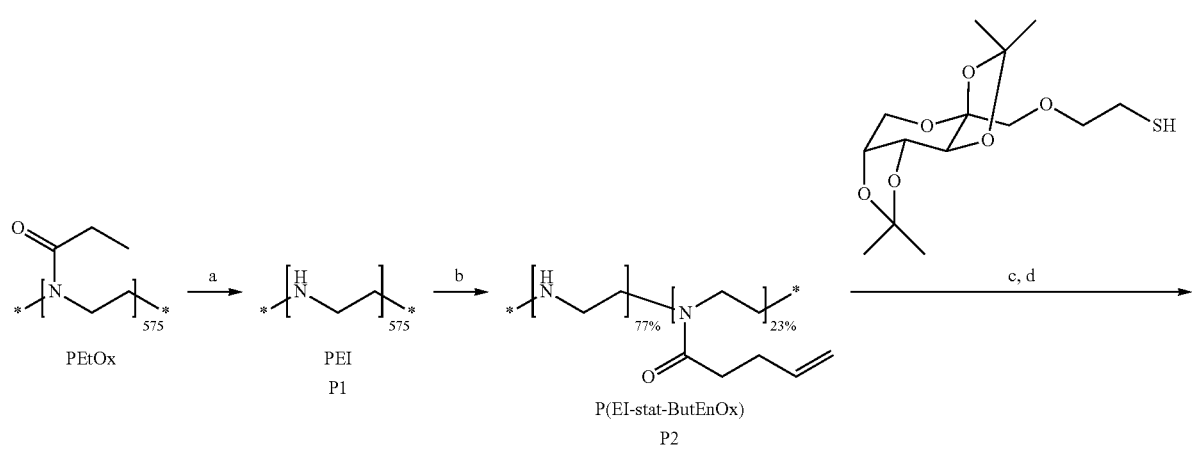

-continued

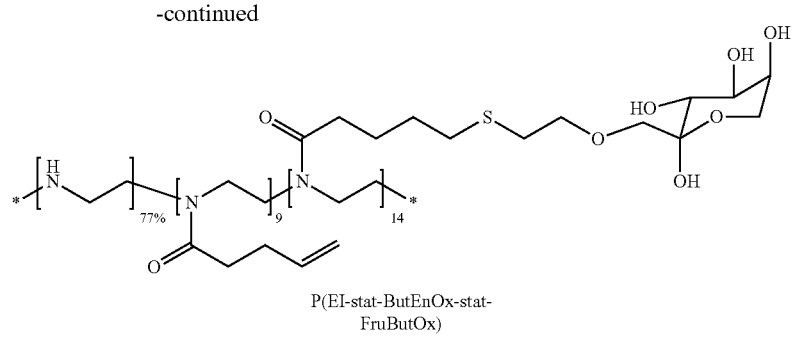

P(EI-stat-ButEnOx-stat-FruButOx)

P3

Schematic representation of the synthesis of P (EI-stat-ButEnOx-stat-FruButOx): a) 6 M HCl, 100° C., reflux; b) pyridine, 4-DMAP, 80° C.; c) D-fructose derivative (5), methanol, 2,2-dimethoxy-2-phenylacetophenone, 25° C., UV=365 nm; d) THF/H$_2$O, 2M HCl, 40° C.

The copolymers and corresponding intermediates have been extensively characterized. As precursor used was a copolymer containing ethyleneimine (EI) and with double bonds functionalized EI. In the last step, the sugar derivative 5 was attached via a photocatalyzed thiol-ene click reaction. Acid deprotection resulted in the water-soluble polymer P3.

(II) Synthesis of D-Fructose Conjugated, Branched Poly (Ethyleneimine) (B-PEI)

1. Synthesis of Epoxy-Functionalized D-Fructose

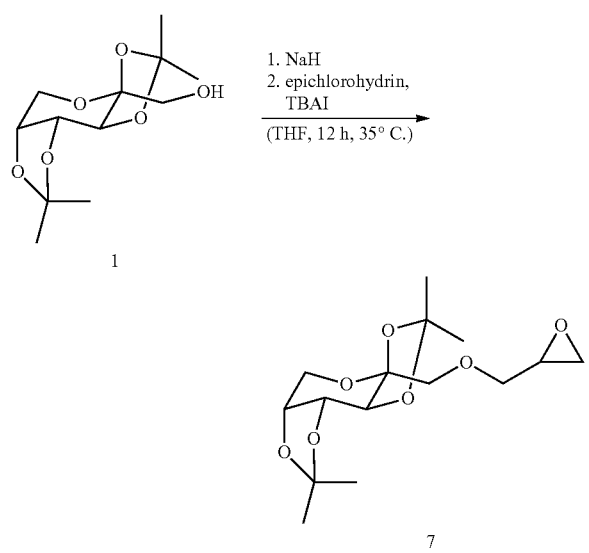

Proceeding from commercially available, isopropylidene-protected D-fructose, Williamson etherification with epichlorohydrin can be used to produce the epoxy-functionalized D-fructose.

2. Coupling of Epoxy-Functionalized D-Fructose with (Branched) B-PEI

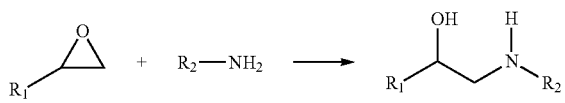

Schematic representation of the general ring-opening reaction between epoxides and primary amines.

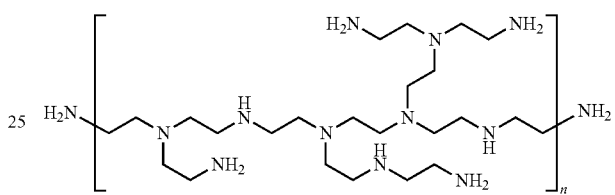

Schematic representation of a possible repeating unit of branched poly (ethyleneimine) (B-PEI).

By stirring at room temperature in methanol for 3 days, B-PEI can be functionalized by a ring-opening reaction with the previously synthesized D-fructose derivative. D-fructose-conjugated B-PEIs were prepared with 14%, 23%, 28%, 39% and 76% functionalized primary amino groups.

3. Cleavage of the Protecting Groups on the Fructose Residues

Acidic cleavage of the isopropylidene protecting groups in the presence of water was carried out after heating the cationic polymers with bound D-fructose derivatives at 40° C. for several days using 2M HCl. Dialysis (cellulose ester, MWCO: 500-1000 Da) against water resulted in D-fructose-functionalized B-PEIs.

The polymer P3 was subjected to intensive, biological evaluation.

a) Cytotoxicity and Hemocompatibility

FIG. 1 shows cell type dependent cytotoxicity studies by alamarBlue assay of polymers P1, P2 and P3. Untreated cells were used as a reference for 100% vitality. The cells were treated for 24 h with the indicated polymer concentrations.

Surprisingly, the D-fructose-conjugated polymer P3 showed increased toxicity to the breast cancer cell line MDA-MB-231, while non-cancer cells (HUVEC and L929) showed no significant reduction in cell vitality. Polymers P2 and P1 showed no selectivity (FIG. 1).

Figure 2A:
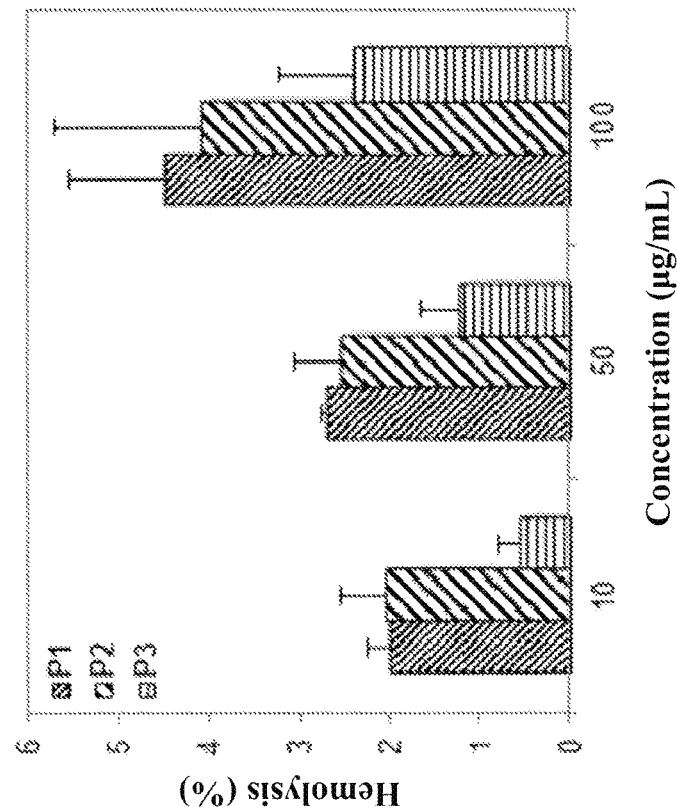
FIG. 2A includes a graph illustrating results of an erythrocyte aggregation assay of polymers P1, P2, and P3 at different concentrations according to embodiments.
Figure 2B:
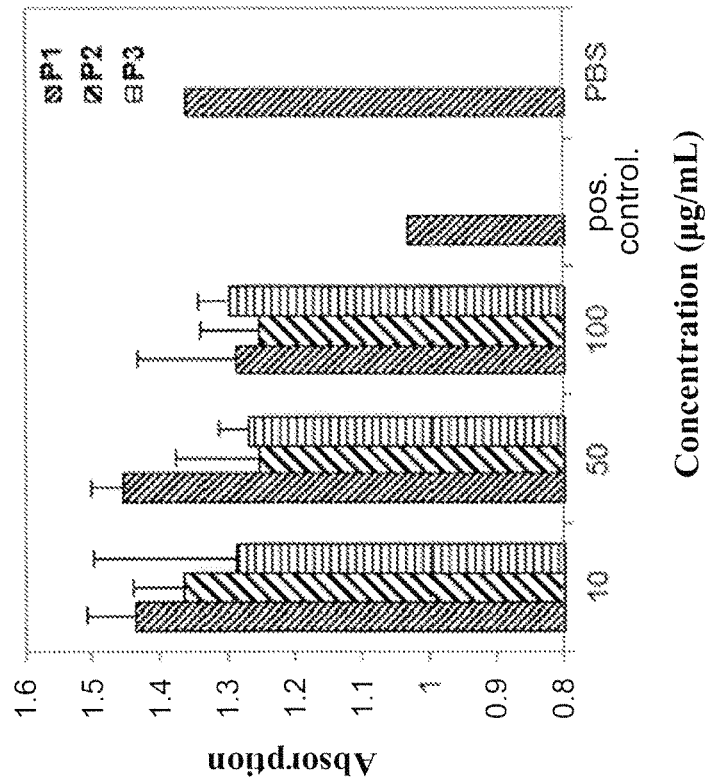
FIG. 2B includes a graph illustrating results of a hemolysis assay of the erythrocytes after incubation with polymers P1, P2, and P3 at different concentrations according to embodiments.

FIG. 2A shows the erythrocyte aggregation assay of the polymers at indicated concentrations. B-PEI was used as a positive control, PBS as a negative control. FIG. 2B shows the hemolysis assay of the erythrocytes after incubation with the polymers at the indicated concentrations. Triton X-100 was used as a positive control (100% hemolysis) and PBS as a negative control (1.99%). A value less than 2% hemolysis is classified as non-hemolytic, 2 to 5% as slightly hemolytic, and >5% as hemolytic. The values represent the mean of three measurements (±standard deviation).

The polymer P3 causes no aggregation of erythrocytes and shows no hemolysis in contrast to P1 and P2 (FIG. 2).

b) Formation Rate and Stability of Polyplex Formation

Figure 3A:
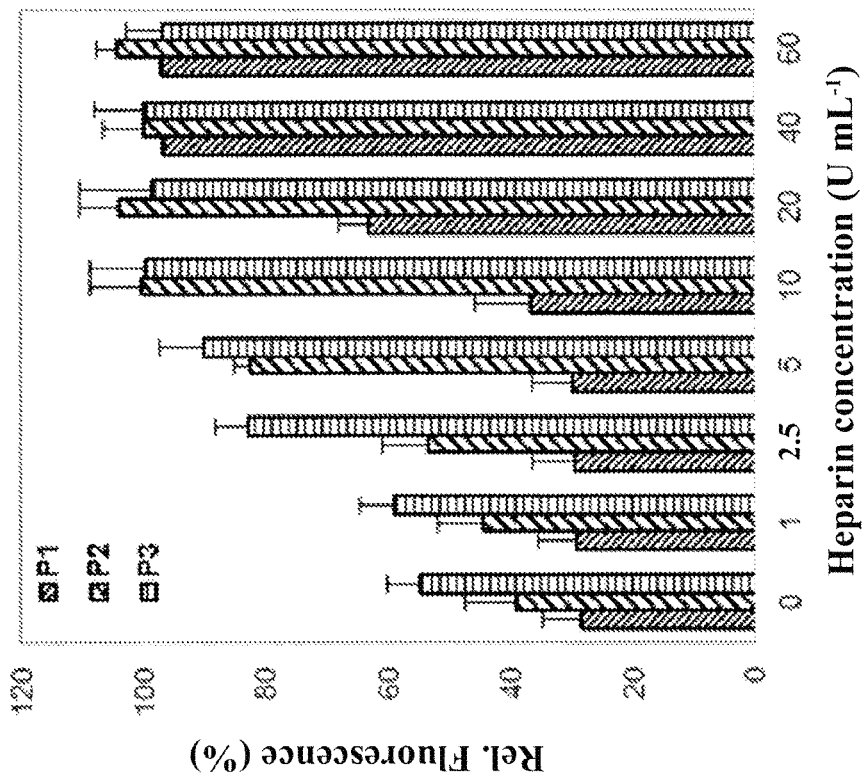
FIG. 3A includes a graph illustrating results of an ethidium bromide quenching assay to show the binding affinity at different N/P ratios leading to polyplex formation according to embodiments.
Figure 3B:
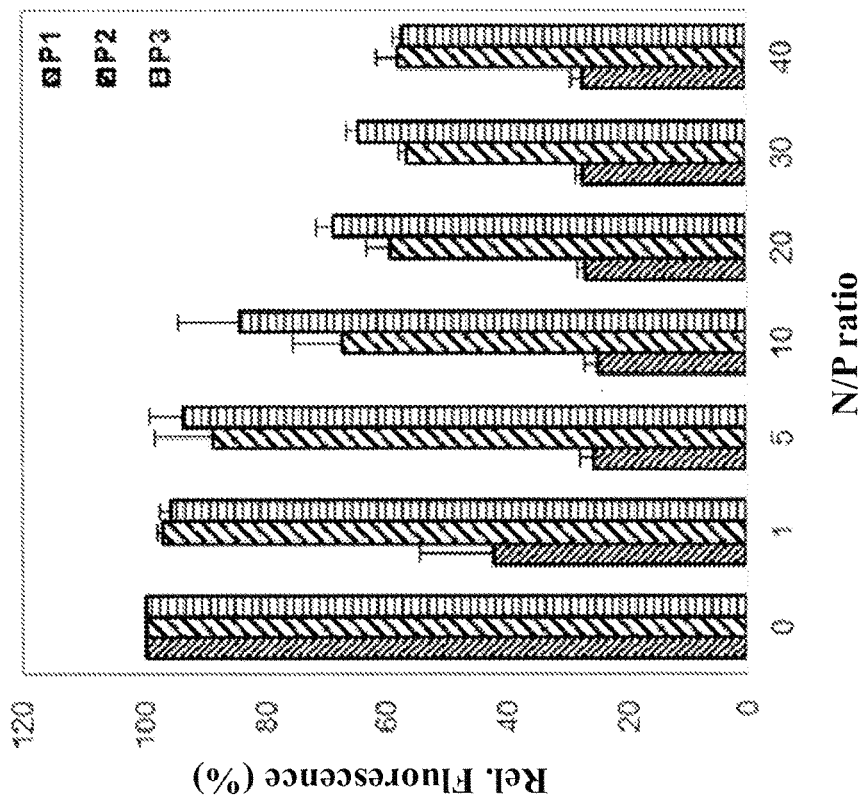
FIG. 3B includes a graph illustrating results of a dissociation assay of polyplexes formed at an N/P ratio of 20 and different heparin concentrations according to embodiments, FIG. 4 includes a graph illustrating results of cell uptake studies by incubating polyplexes of pDNA and polymers P1, P2, and P3 with MDA-MB-231 cells, L929 cells and HUVEC cells according to embodiments.

The ability to complex genetic material is of major interest with respect to the cationic polymer used. To check this, various ratios (N/P ratios) of the sum of all the nitrogen atoms (N) of the cationic polymer and of the phosphorus atoms (P) of the genetic material were tested. FIGS. 3A and 3B show the polyplex formation and stability with pDNA of polymers P1, P2 and P3. FIG. 3A particularly shows the binding affinity at indicated N/P ratios (ethidium bromide quenching assay) and FIG. 3B shows the dissociation assay of the polyplexes at an N/P ratio of 20 using heparin (0 to 60 UmL$^{-1}$). The values reflect the mean of three measurements again ±SD (n=3).

The D-fructose conjugated polymer P3 shows stable polyplex formation at an N/P ratio >15 and further shows rapid release of the genetic material in the presence of heparin (FIG. 3).

c) Size of Polyplexes

| Polymer | Z-average [d/nm] | PDI | Numeric average [d/nm] | Zeta potential [mV] |
|---|---|---|---|---|
| P1 | 217 ± 8 | 0.47 | 71 ± 13 | 24.0 ± 0.4 |
| P2 | 264 ± 11 | 0.35 | 109 ± 33 | 24.3 ± 1.1 |
| P3 | 165 ± 1 | 0.26 | 83 ± 29 | 17.6 ± 0.4 |

The table shows the size and zeta potential of the polyplexes of P1 to P3 at N/P 20 in HBG buffer (measured by dynamic and electrophoretic light scattering).

d) Cell Uptake

To support the results of the cell toxicity studies, the polymers were marked with different dyes (Cy-5 and rhodamine-SCN), incubated with the mentioned cell lines, and the results were evaluated by flow cytometry (FACS) and confocal laser scanning microscopy (CLSM).

Figure 4:
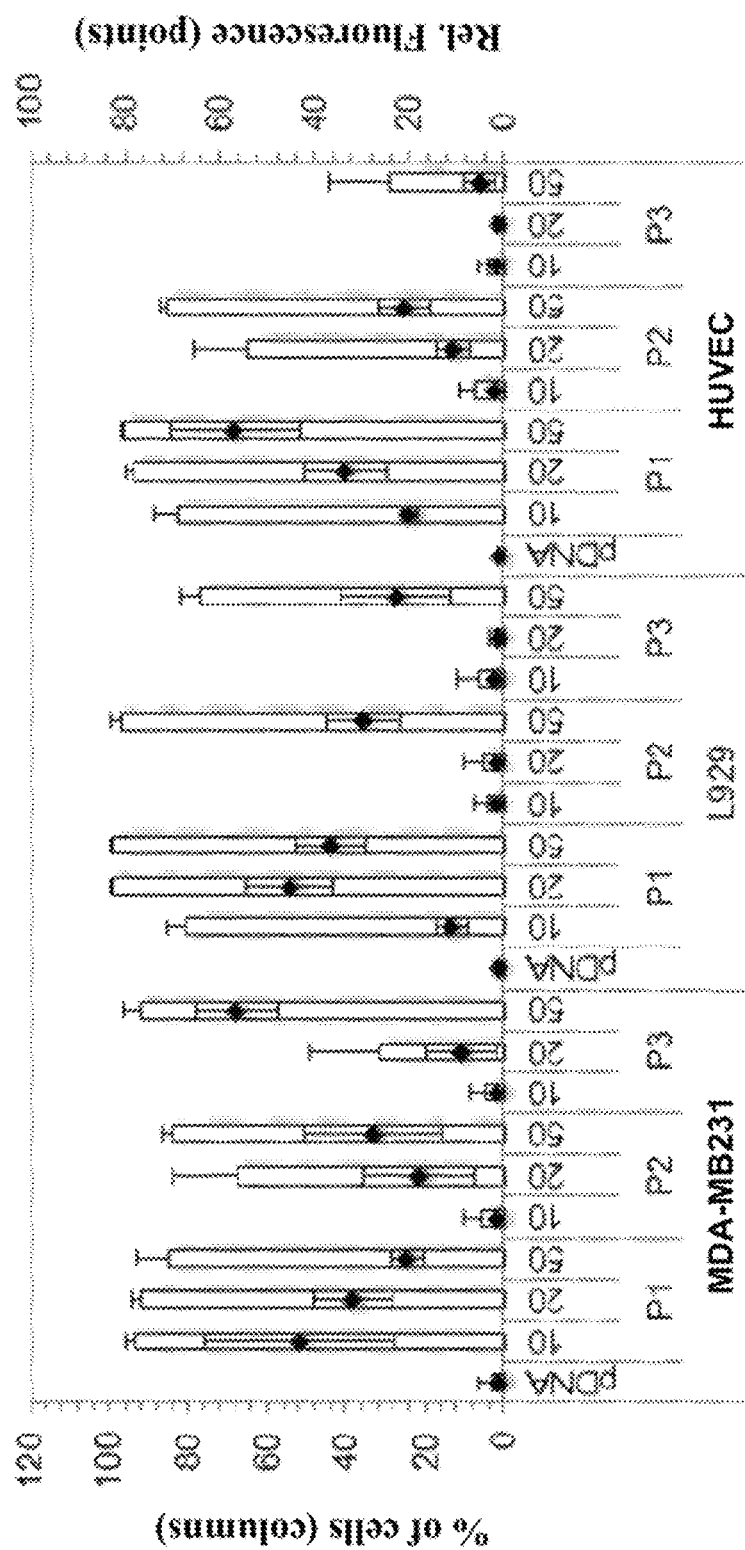
Figure 5:
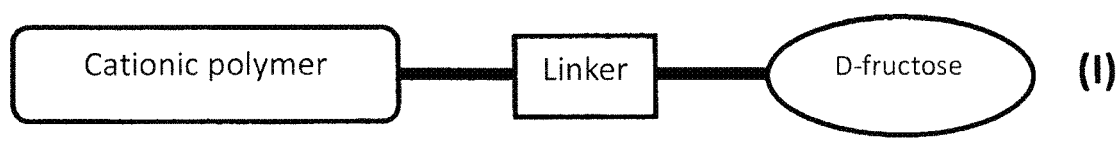
FIG. 5 illustrates general formula (I) of the cationic polymer with covalently bonded D-fructose.

FIG. 4 shows the cell uptake studies. Polyplexes of polymers P1 to P3 were incubated with pDNA marked with YOYO-1, and L929-, HUVEC- and MDA-MB-231 cells. It is shown the relative, mean fluorescence intensity (MFI) of all living cells compared to the pDNA control without polymer (dots). The values reflect the mean of three measurements ±SD (n=3).

P1 and P2 show herein a nonspecific uptake into all cell lines (5-60%) at all N/P ratios. P3, however, shows a significantly increased uptake into the breast cancer cell line MDA-MB-231 for N/P=50 (60%) in comparison to P1 and P2 (20-30%). Furthermore, P3 shows a clearly decreased uptake into the non-breast cancer cell line L929 (20%) and the human primary cell line HUVEC (5%) for N/P=50. The clear difference in uptake behavior in MDA-MB-231 between the immediate precursor P2 and the D-fructose-conjugated P3 underlines a successful targeting function of the sugar molecule. The columns in FIG. 4 reflect the percentage of cells that have fluorescence by pDNA uptake.

These results were also observed by confocal laser scanning microscopy of the cells when incubated with the dye-marked polymers. For N/P 50, the fluorescence intensity of P3 in L929 was low and high in MDA-MB-231 cells, whereas polymers P1 and P2 showed a reverse trend. The results of the uptake studies in living cells are consistent with the results of the cytotoxicity assays and thus show a cell type specificity of the D-fructose-conjugated polymer P3.

What is claimed is:

1. A cationic polymer having covalently bonded D-fructose of the general formula (I) comprising:
    a macromolecular compound of n repeating units having one or more positive charges;
    one or more D-fructose or D-fructose derivative in open-chain, furanoid or pyranoid structure; and
    a linker including one or more linking units linking the macromolecular compound to the one or more D-fructose or D-fructose derivative by an alkyl radical, or an aryl radical, or an alkenyl radical, or an alkynyl radical, or an ether, or a thioether, or an amine, or an ester, or an amide, or another carboxylic acid derivative, or a heterocycle, or a disulfide, or an imine, or an imide,
    wherein the linker covalently links the one or more D-fructose or D-fructose derivative to the macromolecular compound, and the one or more D-fructose or D-fructose derivative is non-glycosidically linked via its carbon atom C1, C3, C4, C5, or C6 to the linker.

2. The cationic polymer having covalently bonded D-fructose according to claim 1, wherein the cationic polymer comprises functional groups which have positive charges under appropriate conditions.

3. The cationic polymer having covalently bonded D-fructose according to claim 1, wherein the cationic polymer comprises functional groups which can carry positive charges at different positions once or several times in the cationic polymer.

4. The cationic polymer having covalently bonded D-fructose according to claim 1, wherein the cationic polymer is a homopolymer or a copolymer.

5. The cationic polymer having covalently bonded D-fructose according to claim 1, wherein the cationic polymer is linear or branched.

6. The cationic polymer of claim 5, wherein the cationic polymer is a branched polymer, the branched polymer being a star polymer, a brush polymer, or a comb polymer.

7. The cationic polymer having covalently bonded D-fructose according to claim 1, wherein the one or more D-fructose or D-fructose derivative are bonded to individual, a plurality of or all repeating units of the macromolecular compound via the linker.

8. The cationic polymer having covalently bonded D-fructose according to claim 1, wherein the one or more D-fructose in addition to free OH groups further comprises a substituent on the carbon atoms 1, 2, 3, 4, 5 and/or 6.

9. The cationic polymer having covalently bonded D-fructose according to claim 1, further comprising a biologically active material selected from the group of nucleic acids, the biologically active material being bonded electrostatically and/or covalently.

10. The cationic polymer having covalently bonded D-fructose according to claim 8, wherein the nucleic acids are selected from the group of DNA, RNA, a ribosome and/or a DNA-RNA hybrid.

11. The cationic polymer of claim 10, wherein the nucleic acids are double stranded or single stranded.

12. The cationic polymer having covalently bonded D-fructose according to claim 1, wherein the cationic polymer is adapted for a transport and a delivery of a biologically active material into a living cell.

13. The cationic polymer having covalently bonded D-fructose according to claim 1, wherein the cationic polymer is adapted for a selective killing of certain cell types.

14. The cationic polymer of claim 1, wherein the one or more D-fructose or D fructose derivative is linked via carbon atom C6 to the linker.

15. The cationic polymer of claim 1, wherein a toxicity of the cationic polymer to cancer cells is greater than a toxicity of the cationic polymer to non-cancer cells.

16. The cationic polymer of claim 15, wherein the cancer cells are breast cancer cells.

17. The cationic polymer of claim 15, wherein the cancer cells are of cell line MDA-MB-231 and the non-cancer cells are HUVEC and L929.

\* \* \* \* \*